United States Patent [19]

Newman

[11] 4,219,193

[45] Aug. 26, 1980

[54] SIMULTANEOUS NECK STRENGTHENER, NECK PROTECTOR, NECK REHABILITATOR

[76] Inventor: Joseph W. Newman, Rte. 1, Box 71-B, Lucedale, Miss. 39452

[21] Appl. No.: 848,308

[22] Filed: Nov. 3, 1977

[51] Int. Cl.² ............................................. A41D 13/00
[52] U.S. Cl. .......................................... 272/94; 2/411; 128/76 R; 128/DIG. 23
[58] Field of Search .................... D2/231, 232; 2/411, 2/413, 414, 415, 416, 2, 2.1 A, 410; 128/133, 134, 80, 97, 76 R, DIG. 23; 272/94

[56] References Cited

U.S. PATENT DOCUMENTS

| | | | |
|---|---|---|---|
| 3,477,426 | 11/1969 | Wincheski | 128/80 |
| 3,522,804 | 8/1970 | Towbin | 2/415 |
| 3,601,123 | 8/1971 | McFarland | 128/DIG. 23 |
| 3,697,065 | 10/1972 | Glassburner | 128/76 R |
| 3,900,896 | 8/1975 | Ackerman | 2/2 |

FOREIGN PATENT DOCUMENTS

| | | | |
|---|---|---|---|
| 480383 | 5/1916 | France | 128/DIG. 23 |
| 627567 | 6/1927 | France | 2/2 |

*Primary Examiner*—Richard J. Johnson
*Attorney, Agent, or Firm*—C. Emmett Pugh & Associates

[57] ABSTRACT

A relatively light, compact and variable neck exerciser which is worn and automatically functions throughout the entire range of neck motion as a result of natural effort an individual performs in his or her particular activity; and simultaneously acts as a neck exerciser and neck protector through the entire range of neck motion during this activity, thereby, being a neck rehabilitator. The device includes a looped spring element fastened, in the case of a football player, between the back of the player's helmet at the apex of the looped spring and the back of the player's shoulder pads at the legs of the looped spring. The spring includes compression, torsion and extention spring sections.

22 Claims, 11 Drawing Figures

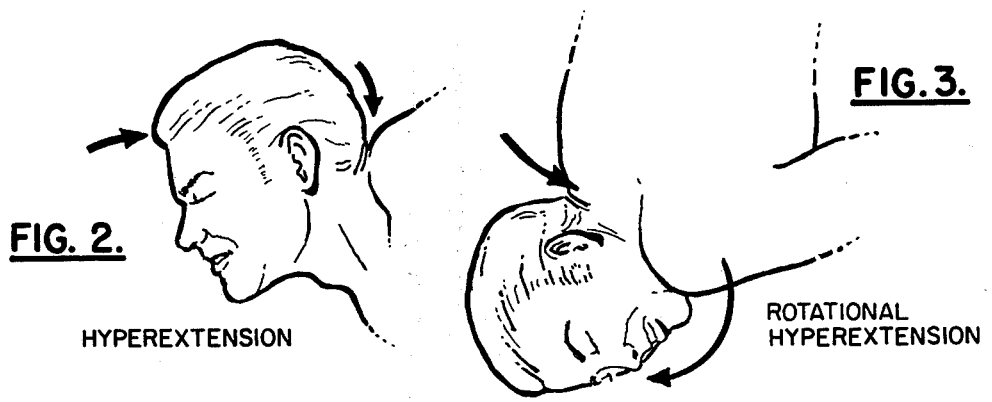
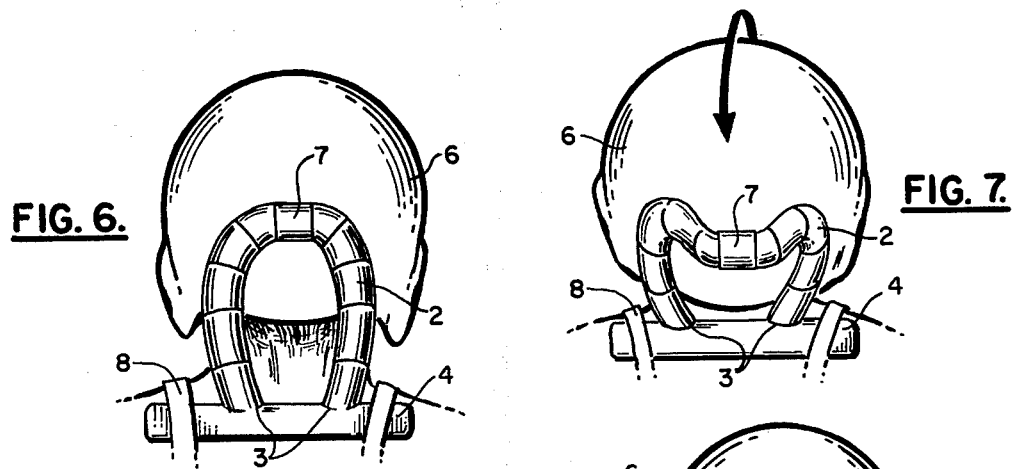
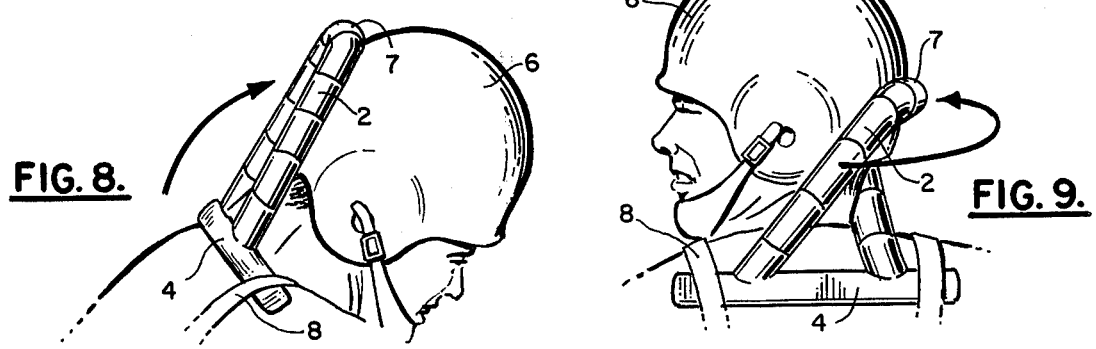

SIMULTANEOUS NECK STRENGTHENER, NECK PROTECTOR, NECK REHABILITATOR

BACKGROUND OF THE INVENTION

1. Field of the Invention

The present invention relates generally to devices for neck exercise and neck protection and, more particularly, to such devices for use in football, vehicle racing, general neck exercise and neck rehabilitation and the like.

2. Description of the Prior Art

On making a patent search I was amazed at the relatively small amount of prior art that pertained to neck exercise, neck protection and neck rehabilitation. The prior art that is shown is not highly efficient in the task that is needed in neck development, protection and rehabilitation.

This is exemplified by the fact that statistical research has confirmed that in football, injuries to the neck are more severe than injuries affecting any other portion of the body. Head and neck injuries have been the cause of more than 95% of football related cases where death or permanent paralysis has occured.

Also, once the neck is injured, there is only very limited exercise performed in the rehabilitation of the neck. This is terrible because the patient should be encouraged to greatly strengthen the neck muscles and take pressure off the spinal cord.

There are neck exercises that can do a good job in strengthening the neck, but they take a special effort and are too time consuming. For example, in football where there are 40 to 60 or more players out for practice, there is an extremely small amount of time available for neck exercise.

D. F. Sims U.S. Pat. No. 3,189,917 shows a neck collar, there was also an inflatable such type neck collar. However, both of these have slack where the head can pivot in all directions before making contact. This allows for whiplash, because of sudden jerks or impact when the neck muscles are relaxed. This happens often in football. Neither of these inventions are worn by many football players today. They are worn mainly by players that have experienced some type neck injury. They do nothing for strengthening of the neck muscles.

G. W. Joseph, Jr. U.S. Pat. No. 3,139,623 and F. J. Mager U.S. Pat. No. 3,230,544 have flaps built in the back of a helmet to allow some direct pressure release. However, they do nothing against whiplash or strengthening of the neck muscles. I don't believe these inventions are used by any football players.

Harry E. Rickard U.S. Pat. No. 3,591,863 shows a spring attached pad that is attached to helmet and rest against the neck. Again, does not satisfactorily prevent neck injury through all of its motions or develope the neck muscles. No wide use in football, if at all.

There is also a patent, namely, Eugene J. Ackerman, U.S. Pat. No. 3,900,896 (issued Aug. 26, 1975), in Class 2 (Catch All) Sub. 2 R that has a leaf spring attached to the helmet and the shoulder pads that also does not protect the neck through all of its motions, or strengthen the neck through all of its motions. Again, not used widely, if at all in football.

All of these inventions are inadequate because the neck is very vulnerable throughout its wide range of motion and an efficient neck protector must cover all of these motions.

Neck injuries in football, considered to be the most serious in nature, usually occur in the cervical vertebrae. The cervical vertebrae are more easily dislocated than the vertebrae in other regions. Cervical injuries resulting in serious injury include fractures, dislocations, and intervertebral disk ruptures. Since the cervical vertebrae are directly protected by the neck and trapezius muscles, one can quickly see the importance of superior neck development for the football player. Therefore, an efficient neck protector should also strengthen the neck muscles throughout its motions.

Referring now to neck rehabilitation, there is C. Bustamate U.S. Pat. No. 2,791,999 that has a hand operated resistance exercise means. This does not strengthen the neck muscles throughout its full range of motions, and concentrated effort is used in its function, where there should be natural effort.

Referring now to neck exercisers in general, there are not any that work the neck muscles throughout its full range of motions without a deliberate concentrated effort. It is well known that the neck and facial muscles are those least used and, therefore, become weak and flabby and unappealing first in the human being. This could be prevented with proper exercise but the average individual will not make a concentrated effort as is needed in such neck exercisers as Feather's U.S. Pat. No. 3,497,217. Therefore, the individual needs a neck exerciser than can be worn and exercises the neck in a natural effort of neck motion.

It is evident from studying the prior art that none anticipated the scope and merit of my invention.

SUMMARY OF THE INVENTION

In the pursuit of my invention, I tried using extension springs and compression springs and leaf springs in the conventional manner and found them to be very inadequate as to desired results. The extension spring will stretch forward, but cannot be compressed. The compression spring can be compressed but not extended easily or twisted easily. The leaf spring can be extended in a line toward 90 degrees from each of two sides of the perpendicular of its axis, but resist strongly the twisting of that axis when secured. The limitations in the conventional manner of springs as a neck protector, neck exerciser and neck rehabilitator are recognized when coupled with Hooke's law, "distortions of elastic material are directly proportional to the distorting force, provided the elastic limit is not exceeded".

If the neck is not exercised through its entire range of motion through full flexion and extension, neck strength obtained will not be functional as the athlete is required to flex and extend his neck through its entire range of motion.

With the foregoing in mind, it is an object of the present invention to obviate the disadvantages of the noted prior art by providing a relatively light, compact, inexpensive, efficient neck exerciser.

Another object of the invention is to provide a neck exerciser to be worn that automatically functions through the entire range of neck motion as a result of a natural effort put out by an individual performing his or her particular activity.

Another object of the invention is to provide a neck exerciser which also functions as a neck protector throughout the full range of neck motion of the individual.

Another object of the invention is to provide a neck exerciser which also functions as a neck rehabilitator throughout the full range of neck motion of the individual.

Another object of the invention is to provide a neck exerciser that will not demand special time just for exercise of the neck muscles.

Another object of the invention is to provide a neck exerciser that allows changing of resistance means as neck muscles change in strength capacity.

This and other objects of the present invention are provided by an extension spring, or other such means, positioned in a novel fashion so as to function as a compression spring, leaf spring and extension spring, thereby, using energy to compress, stretch or twist and resulting in strengthening of the neck muscles and protection of the neck throughout the entire range of neck motion and, thereby, also being a neck rehabilitator.

Other objects and advantages will become obvious to one skilled in the art in light of the following disclosure.

BRIEF DESCRIPTION OF THE DRAWINGS

The novel features of the invention are set out with particularly in the appended claims, but the invention will be understood more fully and clearly from the following detailed description of a preferred embodiment of the invention as set forth in the accompanying drawings, in which:

FIG. 2, FIG. 3, FIG. 4 and FIG. 5 illustrates four different ways that the neck can suffer injury which injuries are prevented by the use of the present invention.

FIG. 6 gives a view of the invention attached to the head and shoulder area of the individual, and looking straight ahead.

FIG. 7 gives a view of the invention when the head is pushed or turned backward.

FIG. 8 gives a view of the invention when the head is pushed or turned forward.

FIG. 9 gives a view of the invention when the head is pushed or turned to the left.

DESCRIPTION OF A PREFERRED EMBODIMENT

Figure 1:
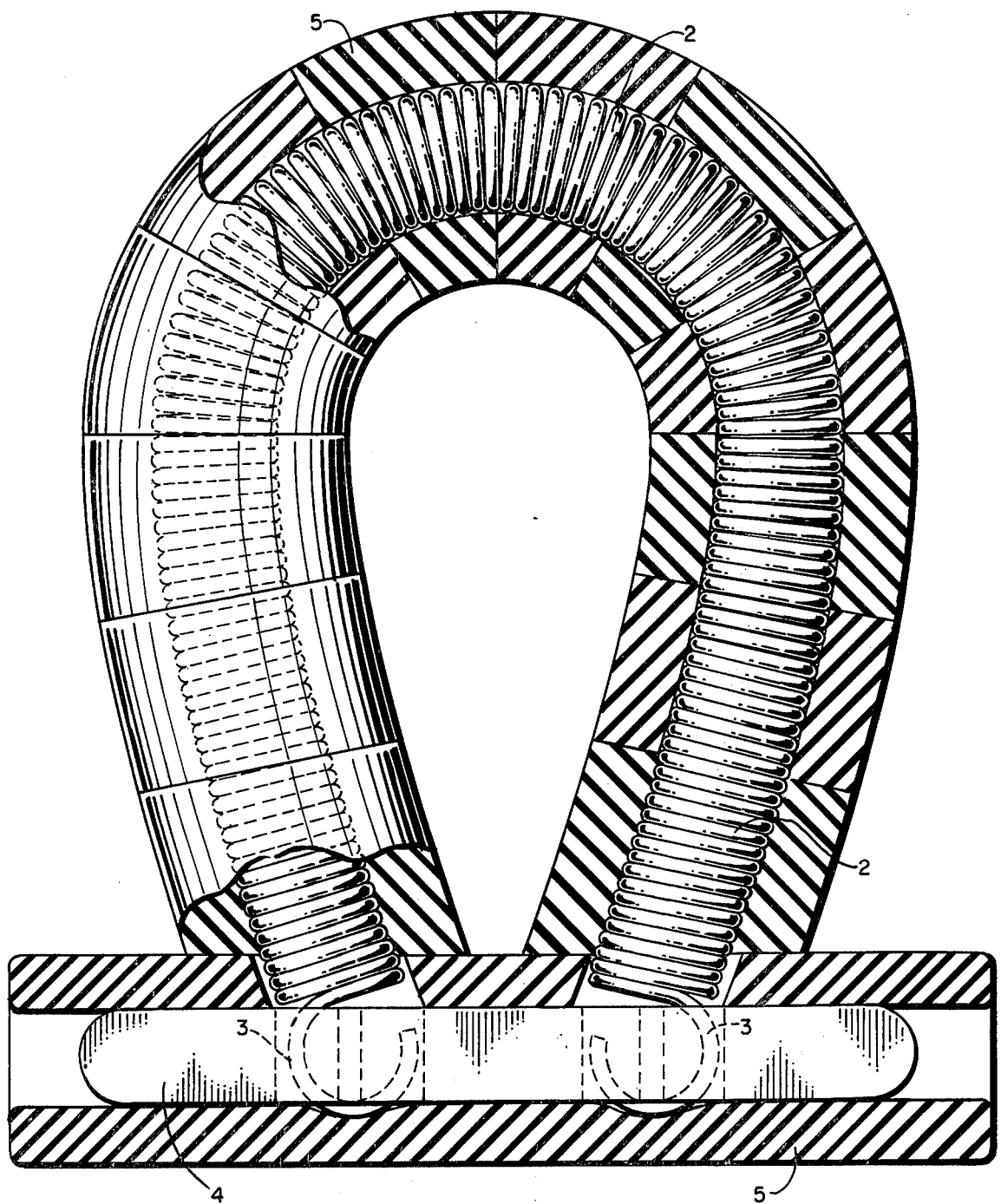
FIG. 1 is a the exact size of full side view of the preferred embodiment of the combination neck exerciser, neck protector and neck rehabilitator according to the present invention, with portions of the cushion material cut away to show the inner spring element.

Referring first to FIG. 1, there is shown the preferred embodiment of the combination neck exerciser, neck protector and neck rehabilitator including an inner spring element 2 according to the present invention to be attached by any of many conventional means to the head and body of the individual. The spring element 2 is shown as an extension spring positioned in a novel fashion, so as to function as an extension spring, compression spring and leaf spring. However, similar results can be achieved by other means, such as for example a solid rubber rod or sheet situated as shown in drawings; inflated rubber sheet or tube situated as shown, whereby, the gas resist being compressed and the rubber resist being stretched; one or more springs so designed where a portion of the spring coils are touching (thereby, acting as extension spring) and the other portion of the coils being spaced apart (thereby, acting as compression spring) then situated to achieve similar results to the inner spring element 2; or a combination of these means as will be explained in more detail hereafter.

Spring element 2 is secured at its ends 3 to an aluminum bar 4 for stability. Similar results can be achieved by having the ends 3 of the spring element 2 joined together. Spring element 2 and bar 4 are covered by any suitable cushion material 5 to protect the individual and make the spring element 2 comfortable to the individual. Spring element 2 can be made of spring materials of different elasticity, whereby, the spring element 2 is easily changed to accommodate the varying strength of individuals as they progress through their particular activity or rehabilitation as is shown in the drawings.

Reference is now made to FIG. 2, FIG. 3, FIG. 4 and FIG. 5 which illustrate, that the neck suffers injury as a result of being forced beyond its structural and anatomical limitations. This is caused in four different ways: Hyperextension, Rotational Hyperextension, Flexion and Whiplash; showing that an efficient invention must protect against all of these dangerous pressure directions and also as a neck exerciser to strengthen the neck muscles throughout these areas, thereby, also being a neck rehabilitator.

With this in mind and, referring now to FIG. 6, spring element is 2 attached to helmet 6 at point 7, which could also be any type securing head harness, with the opposite ends of the spring element 2 attached at securing means 4 to the shoulder or back harness 8 which can be of any suitable design In FIG. 6. The individual is looking straight ahead and there is no resistance at this position.

Referring now to FIG. 7 there is shown a view of the spring element 2 when the head and helmet 6 are pushed or turned backward, thereby, expanding the spring element 2 in width and at the same time compressing spring element 2 in height, thereby, bracing the individual's head at the sides as well as at the top. Looking back at FIG. 2 the benefits of the invention are easily seen. There is a noticeable comfortable increase in pressure throughout this movement.

Referring now to FIG. 8 there is shown a view of the spring element 2 when the head and helmet 6 are pushed or turned forward, thereby, stretching the spring element 2 in an elongated direction and, thereby, bracing the individual's head from this forward movement. Looking back now to FIG. 4 and FIG. 5, the benefits of the invention are again easily seen. There is a noticeable comfortable increase in pressure throughout this movement as well.

Referring now to FIG. 9, there is shown a view of the invention when the head and helmet 6 are pushed or turned to the left, thereby, stretching and twisting the spring element 2 in the form similar to a figure eight as the head is pivoted to greater degrees; thereby, bracing the individual's head from this sideward movement. Looking back now to FIG. 3, the benefits of the invention are again easily seen. There is a noticeable comfortable increase in pressure throughout this movement as well.

Figure 10:
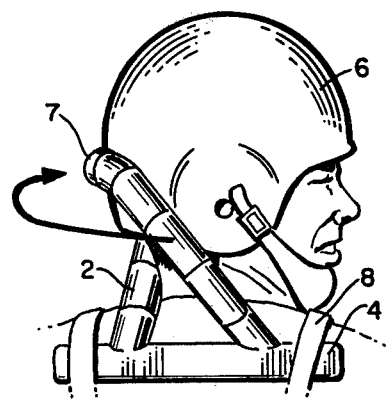
FIG. 10 gives a view of the invention when the head is pushed or turned to the right.

Referring now to FIG. 10, there is shown a view of the spring element 2 when the head and helmet 6 are pushed or turned to the right, thereby, giving the same results as in FIG. 9, but twisting the spring element 2 in the opposite direction. Looking back again at FIG. 3, the benefits of the invention are easily seen. There is again a noticeable comfortable increase in pressure throughout this movement.

Looking back now at FIG. 6 and FIG. 7 together, the innovation of the spring element invention 2, an extension spring, giving the results of a compression spring can be understood. When the head and helmet 6 are pushed backward, pressure is applied to the spring element 2 at the point of attachment 7, which is then transferred throughout the invention 2, thereby, causing the point 7 to pull and stretch the top of the two legs 3 of the spring element 2 inward, thereby, causing the balance of the two legs 3 to be pushed off center and stretched outward, whereby, the spring element 2 is being stretched in several directions simultaneously and giving the same results or superior to that of conventional compression spring. FIG. 8, FIG. 9 and FIG. 10 are now self explanatory as to the spring element 2 reacting as an extension spring and a leaf spring.

Figure 11:
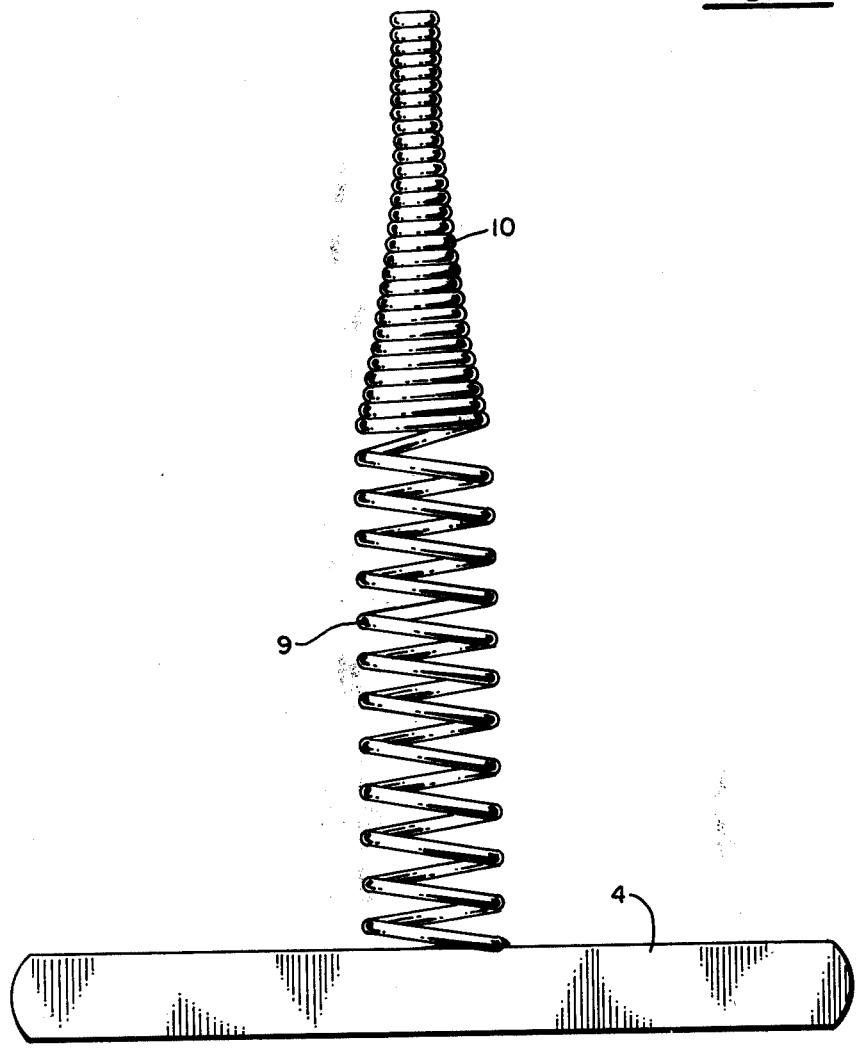
FIG. 11 gives a side view of another embodiment of the invention.

FIG. 11 shows a modification of the invention showing similar results obtained using a spring or springs so turned as to have one part acting as a conventional compression spring 9 and the other part acting as a conventional extension spring 10, with one end attached to the head and the other end to the shoulder area as previously shown. It is now seen that similar results could be achieved throughout the previous shown motions (FIGS. 6–10), so as to give the results of conventional compression, leaf and extension springs, thereby, becoming a neck exerciser, neck protector and neck rehabilitator.

Although the present invention has been illustrated in terms of a preferred embodiment, it will be obvious to one of ordinary skill in the art that numerous modifications may be made (such as has been pointed out in description of FIG. 1 of the invention) without departing from the true spirit and scope of the invention which is limited only by the appended claims.

I claim:

1. A neck device for resisting movement of the head and for wearing between head gear on the head of the user and the upper torso of the user comprising:
a force resisting, elastic element including a first, compression section which resists a force tending to compress said first section, and a second, extension section which resists a force tending to extend said second section, and a third twistable section which resists a force tending to twist said third section, said force resisting, elastic element being attached at its upper end to the head gear of the user and having at its lower end laterally spaced attachment means for attachment to the upper torso of the user, with said first and second sections being located at least in part between the points of attachment to the headgear and between the user's shoulders, said force resisting, elastic element being positioned when attached to the user being centrally located with respect to the neck of the user, said force resisting, elastic element resisting movement of the user's head in moving forward, backward and turning sideways from a neutral position of the head being upright and looking forward.

2. A device as recited in claim 1, wherein said elastic element is easily changeable to accommodate the varying in neck muscle strength of individuals as they progress through their particular activity or rehabilitation.

3. A device as recited in claim 1, wherein said elastic element is easily and quickly detachable at one end, from either or both the head securing means and the shoulder or back securing means, thereby, allowing for complete freedom of neck movement.

4. A device as recited in claim 1, wherein said elastic element consist of a singular extension spring positioned in an unusual fashion so as to function as a compression spring, torsion spring and extension spring, thereby, using energy to compress, stretch or twist.

5. A device as recited in claim 1, wherein said elastic element comprises at least one spring so designed where a portion of each spring coils are touching (thereby, acting as extension spring) and the other portion of each spring coils being spaced apart (thereby, acting as a compression spring).

6. A device as recited in claim 1, wherein said elastic element comprises an inflated elastic structure, the gas resist being compressable (acting as compression spring) and the structure being stretchable (acting as an extension spring).

7. A device as recited in claim 1 wherein said elastic element comprises a solid elastic structure.

8. The device of claim 1 wherein the device is a protective device and the user is a football player wearing a helmet and wherein the force resisting, elastic element is attached to the rear of the helmet.

9. A device as recited in claim 1, wherein said elastic element is covered by a suitable cushion material to protect the user and make the device comfortable to the user.

10. A device as recited in claim 1, wherein said elastic element is relatively light, compact and inexpensive.

11. The device of claim 1 wherein said force resisting, elastic element is in a neutral state and applies no significant force to the head of the user when the user's head is upright and looking straight ahead.

12. The device of claim 1 wherein said force resisting elastic element is located behind the head of the user and wherein said first, compression section resists the movement of the user's head when it moves backward from its upright position, said second, extension section resists the movement of the user's head as it moves forward from its upright position, and said third, twistable section resists the movement of the user's head as it turns to either side from its staight forward position.

13. The device of claim 1 wherein said first and second sections are located in line with one another.

14. The device of claim 13 wherein said element includes a first compression spring section in which the spirals of the spring are separated in their natural state and a second extention section in which the spirals of the spring are in contact with one another in their natural state.

15. The device of claim 1 wherein said force resisting, elastic element comprises at least one spring.

16. The device of claim 15 wherein said elastic element comprises one continuous spring adapted, positioned and configured to form said three sections.

17. The device of claim 15 wherein said spring is looped to form an inverted "U" configuration, with the apex of the loop being attached to the back of the head of the user and the two legs of the loop being attached to the back of the user.

18. The device of claim 17 wherein there is further included a horizontally disposed bar to which said two legs are attached, the bar being attached to the back of the user.

19. The device of claim 17 wherein said apex is centrally located behind the center of the back of the user's head.

20. The device of claim 15 wherein there is further included cushion material surrounding said spring.

21. The device of claim 15 wherein said elastic element further includes the action of a torsion spring section.

22. The method of protecting the neck of a football player from neck injuries such as, for example, hyperextension, rotational hyperextension, flexion and whiplash, comprising the following steps:
 (a) providing a neck device for resisting movement of the player's head which includes a force resisting elastic element having a first, compression section which resists a force tending to compress said first section, a second, extension section which resists resists a force which tends to extend said second section, and a third, twistable section which resists a force which tends to twist said third section;
 (b) attaching the upper portion of said elastic element to the player's helmet at the back thereof and attaching the lower portion of said elastic element to the back of the player, with said first and said second sections positioned at least in part behind the neck of the player; and
 (c) allowing said compression section to compress with some resistance when the player's head moves backward from its upright position;
 (d) allowing said extension section to extend with some resistance when the player's head moves forward from its upright position; and
 (e) allowing said twistable section to twist with some resistance when the player's head is turned to either side from its straight forward position, the various force resisting sections protecting the neck of the player from sudden violent movements.

* * * * *